(12) United States Patent
Lewke

(10) Patent No.: US 8,035,398 B1
(45) Date of Patent: Oct. 11, 2011

(54) ARRANGEMENT TO DETECT A FAULT ELECTRICAL CONNECTION

(75) Inventor: Bastian Lewke, Herning (DK)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 13/093,891

(22) Filed: Apr. 26, 2011

(30) Foreign Application Priority Data

May 5, 2010 (EP) .................................. 10161991

(51) Int. Cl.
*G01R 31/04* (2006.01)

(52) U.S. Cl. ....................................................... 324/538

(58) Field of Classification Search .................. None
See application file for complete search history.

(56) References Cited

U.S. PATENT DOCUMENTS

| | | |
|---|---|---|
| 2008/0167754 A1 | 7/2008 | McAllister et al. |
| 2009/0058086 A1 | 3/2009 | Arinaga et al. |
| 2010/0276930 A1* | 11/2010 | Fortmann ........................ 290/44 |
| 2011/0133743 A1* | 6/2011 | Barton ........................... 324/415 |

FOREIGN PATENT DOCUMENTS

JP  2001287396 A  10/2001

* cited by examiner

*Primary Examiner* — Jermele M Hollington

(57) ABSTRACT

An arrangement to detect a fault electrical connection in a wind turbine is provided. According to the arrangement, an ozone sensor is located close to a dedicated electrical connection within the wind turbine. A certain amount of ozone gas, which is generated by a corona due to a fault of the dedicated electrical connection, is detected by the ozone sensor.

4 Claims, 1 Drawing Sheet

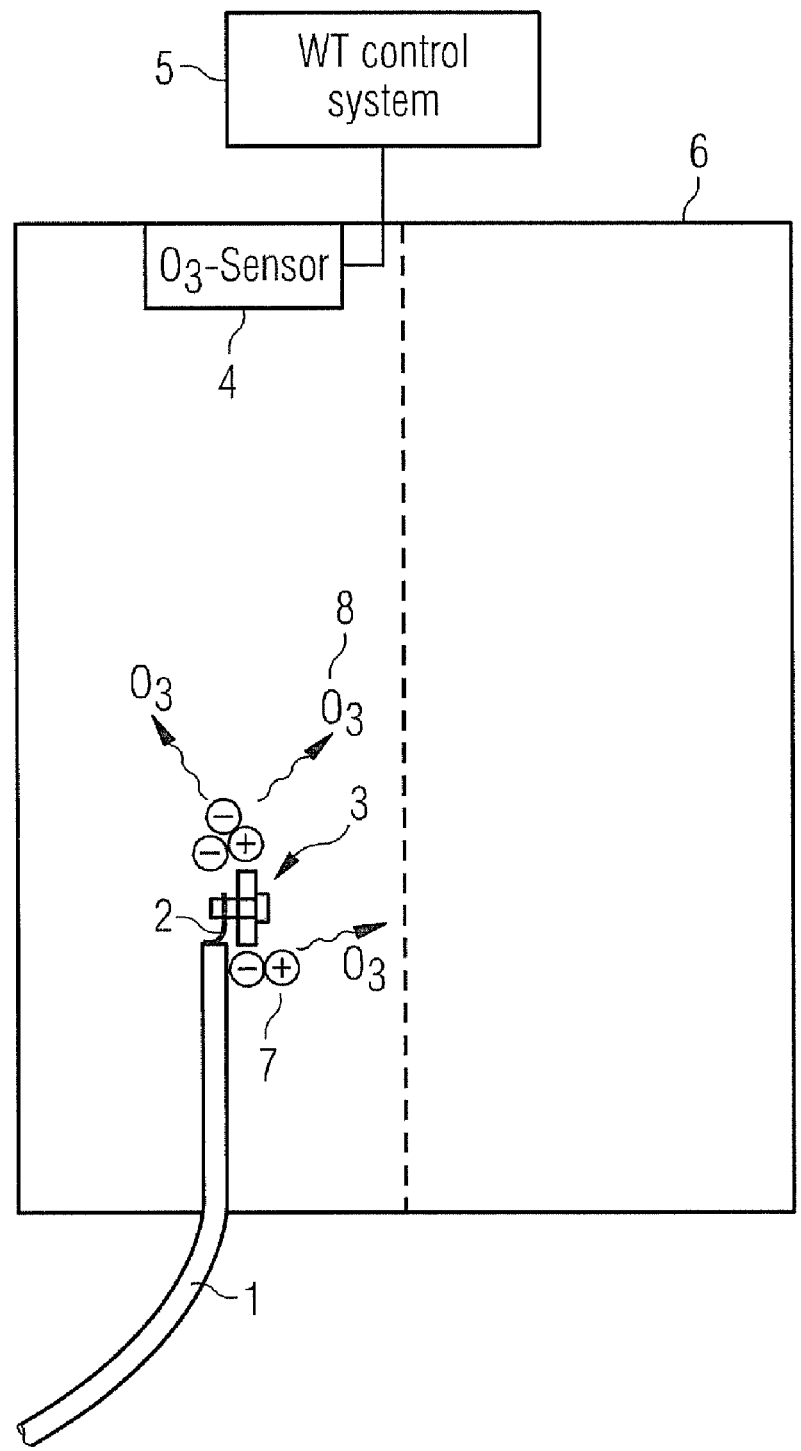

ARRANGEMENT TO DETECT A FAULT ELECTRICAL CONNECTION

CROSS REFERENCE TO RELATED APPLICATIONS

This application claims priority of European Patent Office Application No. 10161991.4 EP filed May 5, 2010, which is incorporated by reference herein in its entirety.

FIELD OF INVENTION

The invention relates to an arrangement to detect a fault electrical connection in a wind turbine.

BACKGROUND OF INVENTION

Wind turbines are high tech facilities and are equipped with various electrical components like a control system, a converter, a transformer or with an extensive cabling.

Especially offshore wind turbines are placed in a harsh environment and thus far away from a service hub. Due to the environmental forces, dynamic mechanical loads, vibrations and due to movements, which all acts on the wind turbine, electrical connections of the wind turbine might become loose and thus fault connections may occur.

A fault electrical connection increases electrical losses and might lead to fire in the wind turbine, in a worst case scenario, as electrical losses are transferred into heat.

Smoke detectors are used to detect fire as soon as it emerges, but this point of time may be too late to save the wind turbine from destruction.

SUMMARY OF INVENTION

It is an object of the invention to provide an improved arrangement to detect fault electrical connections in a reliable and easy way to prevent the development of fire in a wind turbine. This object is solved by an arrangement as claimed in the independent claim. Preferred embodiments are object of the dependent claims.

According to the arrangement, a fault of an electrical connection in a wind turbine is detected. An ozone sensor is located close to a dedicated electrical connection within the wind turbine. A certain amount of ozone gas, which is generated by a corona due to a fault of the dedicated electrical connection, is detected by the ozone sensor.

Due to this the risk of an emerging fire is detected quite soon and appropriate steps are taken to prevent further damages.

For example the area affected within the wind turbine may be flooded by a gas like helium. Helium is used to extinguish an emerging fire or is even used that fire can emerge at all.

It is also possible to distribute a certain and maybe optimized amount of "fire-extinguishing-fluids" or appropriate gases to prevent or blow out the fire within the wind turbine.

The wind turbine contains volumes, which are nearly closed in view to the ambient or in view to the environment of the wind turbine—the nacelle for example.

Preferably the sensor is located in this volumes, thus the sensor is isolated from the ambient air. Due to this the sensor is not sensitive to environmental circumstances or impacts like ultraviolet radiation for example, which may originate ozone, too.

Preferably the ozone sensor is protected by a kind of cover or shell against remaining ambient impacts if needed.

The arrangement invented is very cheap as ozone sensors are widely used in other technical fields—like meteorology, for example.

The arrangement invented is easy to be installed, as there are a lot of "ready to be implemented solutions" available on the market.

BRIEF DESCRIPTION OF THE DRAWINGS

The invention is shown in more details by help of a FIGURE.

FIG. 1 shows the arrangement invented.

DETAILED DESCRIPTION OF INVENTION

A cable 1 is connected with a cable terminal 3 via a cable connection 2. The cable connection 2 may be realized as a joint with a screw or the like, for example.

Due to this type of connection 2 the connection-arrangement 2 may be weak in view to its electrical parameters.

The cable 1 may be a so called "LV-cable", but any other cable may be secured and checked by the arrangement invented.

An ozone sensor 4 is located close to the cable connection 2. The cable connection 2 and the ozone sensor 4 are preferably located into a shell 6 or into a housing 6.

The housing or shell may be cubical. The housing or shell ensures that the sensor 4 is not influenced by environmental effects or that the sensor is not disturbed in view to the ozone measurement intended.

Preferably the arrangement invented is used to check cables of a controller or of a converter—not shown here in detail.

Preferably the ozone sensor 4 is connected with a wind turbine control system 5. This enables the wind turbine to signal an alert if needed. The alert might be sent to a remote controller for example.

Due to the weak cable connection 2 a corona 7 will be emanated by the current, which is guided through the cable 1 and the cable connection 2.

Due to the corona 7 ozone gas 8 is generated. The ozone gas 8 will be detected by the ozone sensor 4 according to the invention.

The invention claimed is:

1. Arrangement to detect a fault electrical connection in a wind turbine, comprising:
   an ozone sensor located close to a dedicated electrical connection within the wind turbine,
   wherein an ozone gas, which is generated by a corona due to a fault of the dedicated electrical connection, is detected by the ozone sensor.

2. The arrangement according to claim 1, wherein the ozone sensor is controlled remotely.

3. The arrangement according to claim 1, wherein the ozone sensor is covered or enclosed by a shell or housing in order to prevent that ambient influences interfere with an detection of the ozone gas.

4. The arrangement according to claim 2, wherein the ozone sensor is covered or enclosed by a shell or housing in order to prevent that ambient influences interfere with an detection of the ozone gas.

* * * * *